US00PP18418P2

(12) United States Plant Patent
Bolwell

(10) Patent No.: US PP18,418 P2
(45) Date of Patent: Jan. 15, 2008

(54) ***GAZANIA* PLANT NAMED 'SUGA119'**

(50) Latin Name: *Gazania hybrida*
Varietal Denomination: Suga119

(75) Inventor: Narelle Gai Bolwell, Picton (AU)

(73) Assignee: NuFlora Intl. Pty. Ltd., Macquarie Fields, NSW (NL)

( * ) Notice: Subject to any disclaimer, the term of this patent is extended or adjusted under 35 U.S.C. 154(b) by 0 days.

(21) Appl. No.: 11/521,151

(22) Filed: Sep. 14, 2006

(51) Int. Cl.
*A01H 5/00* (2006.01)

(52) U.S. Cl. ..... Plt./334

(58) Field of Classification Search ..... Plt./334
See application file for complete search history.

*Primary Examiner*—Kent Bell
*Assistant Examiner*—Annette Para
(74) *Attorney, Agent, or Firm*—C. A. Whealy

(57) ABSTRACT

A new and distinct cultivar of *Gazania* plant named 'Suga119', characterized by its compact, outwardly spreading, low-growing and mounded plant habit; freely branching growth habit; freely flowering habit; large anemone-type inflorescences with orange-colored ray florets; and good garden performance.

1 Drawing Sheet

Botanical designation: *Gazania hybrida.*
Cultivar denomination: 'Suga119'.

BACKGROUND OF THE INVENTION

The present invention relates to a new and distinct cultivar of *Gazania* plant, botanically known as *Gazania hybrida* and hereinafter referred to by the name 'Suga119'.

The objective of the breeding program is to create new *Gazania* cultivars with desirable and unique inflorescence form and floret colors.

The new *Gazania* originated from a cross-pollination in Cobbitty, New South Wales, Australia in January, 2001, of a proprietary selection of *Gazania hybrida* identified as code number KO4, not patented, as the female, or seed, parent with a proprietary selection of *Gazania hybrida* identified as code number PS20.5, as the male, or pollen, parent. The new *Gazania* was discovered and selected by the Inventor as a single flowering plant within the progeny of the stated open-pollination in a controlled environment Cobbitty, New South Wales, Australia in October, 2002.

Asexual reproduction of the new *Gazania* by vegetative tip cuttings in a controlled environment in Cobbitty, New South Wales, Australia since October, 2002, has shown that the unique features of this new *Gazania* are stable and reproduced true to type in successive generations.

SUMMARY OF THE INVENTION

Plants of the cultivar Suga119 have not been observed under all possible environmental conditions. The phenotype may vary somewhat with variations in environment such as temperature and light intensity, without, however, any variance in genotype.

The following traits have been repeatedly observed and are determined to be the unique characteristics of 'Suga119'. These characteristics in combination distinguish 'Suga119' as a new and distinct potted *Gazania* cultivar:

1. Compact, outwardly spreading, low-growing and mounded plant habit.
2. Freely branching growth habit.

3. Freely flowering habit.
4. Large anemone-type inflorescences with orange-colored ray florets.
5. Good garden performance.

Plants of the new *Gazania* differ from plants of the female parent selection primarily in inflorescence type as plants of the female parent selection have daisy-type inflorescences. Plants of the new *Gazania* differ from plants of the male parent selection primarily in ray floret color as plants of the male parent selection have yellow-colored ray florets.

Plants of the new *Gazania* can be compared to plants of the *Gazania* cultivar Sunset Jane, not patented. In side-by-side comparisons conducted in Cobbitty, New South Wales, Australia, plants of the new *Gazania* differed primarily from plants of the cultivar Sunset Jane in ray floret coloration as plants of the cultivar Sunset Jane had amber-colored ray florets.

BRIEF DESCRIPTION OF THE PHOTOGRAPHS

The accompanying photographs illustrate the overall appearance of the new *Gazania.* These photographs show the colors as true as it is reasonably possible to obtain in colored reproductions of this type. Colors in the photographs may differ slightly from the color values cited in the detailed botanical description which accurately describe the colors of the new *Gazania.*

The photograph on at the bottom of the sheet comprises a side perspective view of a typical flowering plant of 'Suga119' grown in a container.

The photograph at the top of the sheet is a close-up view of a typical inflorescence of 'Suga119'.

DETAILED BOTANICAL DESCRIPTION

The aforementioned photographs and following observations and measurements describe plants grown during the late winter and early spring in Encinitas, Calif. and under conditions and practices which approximate those generally used in commercial potted *Gazania* production. Plants were initially grown in a polyethylene-covered greenhouse and then grown for the last three weeks in an outdoor nursery. During the production of the plants, day temperatures averaged 24° C. and night temperatures averaged 19° C. Plants used in the photographs and for the description were about 18 weeks old. In the following description, color references are made to The Royal Horticultural Society Colour Chart, 1995 Edition, except where general terms of ordinary dictionary significance are used.

Botanical classification: *Gazania hybrida* cultivar Suga119.

Parentage:

*Female, or seed, parent.*—Proprietary selection of *Gazania hybrida* identified as code number KO4, not patented.

*Male, or pollen, parent.*—Proprietary selection of *Gazania hybrida* identified as code number PS20.5, not patented.

Propagation:

*Type.*—Terminal cuttings.

*Time to initiate roots, summer.*—About ten days at temperatures of about 20° C.

*Time to initiate roots, winter.*—About twelve days at temperatures of about 18° C.

*Time to produce a rooted young plant, summer.*—About 38 days at temperatures of about 20° C.

*Time to produce a rooted young plant, winter.*—About 42 days at temperatures of about 18° C.

*Root description.*—Fine, fibrous; white in color.

*Rooting habit.*—Freely branching; dense.

Plant description:

*Appearance.*—Herbaceous anemone-type potted *Gazania*. Compact, outwardly spreading, low-growing and mounded plant habit. Strong and freely branching growth habit with about twelve lateral branches per plant. Vigorous growth habit.

*Plant height.*—About 13 cm.

*Plant width.*—About 31.5 cm.

*Lateral branches.*—Length: About 15 cm. Diameter: About 1.2 cm. Internode length: About 1.2 cm. Strength: Strong. Texture: Minute pubescence. Color: 145C.

Foliage description:

*Arrangement.*—Alternate, simple.

*Length.*—About 7.8 cm.

*Width.*—About 6.2 cm.

*Shape.*—Deeply dissected with nine lobes.

*Apex.*—Broadly acute.

*Base.*—Attenuate.

*Margin.*—Deeply indented; entire.

*Texture, upper surface.*—Smooth, glabrous.

*Texture, lower surface.*—Pubescent, flocculent.

*Venation pattern.*—Parallel.

*Color.*—Developing foliage, upper surface: 144A. Developing foliage, lower surface: 196D. Fully expanded foliage, upper surface: 147A; venation, 148C. Fully expanded foliage, lower surface: 194D; venation, 147C.

*Petiole length.*—About 6.6 cm.

*Petiole diameter.*—About 5 mm.

*Petiole texture, upper surface.*—Smooth, glabrous.

*Petiole texture, lower surface.*—Pubescent, flocculent.

*Petiole color, upper surface.*—147C.

*Petiole color, lower surface.*—148C.

Inflorescence description:

*Appearance.*—Anemone-type inflorescence form with ligulate-shaped ray florets. Inflorescences borne on terminals above foliage. Disk and ray florets arranged acropetally on a capitulum. Inflorescences not fragrant.

*Flowering season.*—Plants flower from spring to early fall in Southern California; flowering continuous during this period.

*Inflorescence longevity.*—Inflorescences last about three to five days on the plant; inflorescences persistent.

*Quantity of inflorescences.*—About 25 inflorescences develop per plant.

*Inflorescence bud.*—Height: About 3.4 cm. Diameter: About 1.6 cm. Shape: Ovoid, pointed. Color: 162A.

*Inflorescence size.*—Diameter: About 7.5 cm. Depth (height): About 2.5 cm. Diameter of disc: About 3.5 cm. Receptacle height: About 2.3 cm. Receptacle diameter: About 3 cm.

*Ray florets.*—Shape: Ligulate. Orientation: Initially upright, then about 30° from vertical, outer ray florets perpendicular to peduncle; reflexing. Length: About 3.7 cm. Width: About 1 cm. Apex: Acute or emarginate. Base: Acute. Margin: Entire. Texture, upper and lower surfaces: Smooth, glabrous, satiny. Number of ray florets per inflorescence: About 22 in a single whorl. Color: When opening, upper surface: Darker and brighter than 24A. When opening, lower surface: 18A; thin longitudinal stripes, 145D. Fully opened, upper surface: Darker and brighter than 25A; spot towards the base, 10A and 166A. Fully opened, lower surface: 13C; streak at the apex, 187A; towards the margins, 23B; thin longitudinal stripes, 145B.

*Disc florets.*—Arrangement: Massed at center of receptacle. Shape: Tubular, elongated, enlarged. Apex: Five-pointed. Length: About 2.3 cm. Width, at apex: About 9 mm. Width, at base: About 1 mm. Number of disc florets per inflorescence: About 170. Color: Immature: 15C tinged with 145B. Mature: Apex: Brighter than 25A; towards the apex, 17A. Mid-section: 15B. Base: 1D.

*Phyllaries.*—Number of phyllaries per inflorescence: About 46 in about three or four whorls. Length: About 1.5 cm. Width: About 3 mm. Shape: Linear to elliptical. Apex: Acuminate. Base: Fused. Margin: Entire. Texture, upper surface: Smooth, glabrous. Texture, lower surface: Minute pubescence. Color, upper surface: 146C. Color, lower surface: 148A.

*Peduncles.*—Length, terminal peduncle: About 14.5 cm. Length, second peduncle: About 9 cm. Diameter: About 3.5 mm. Angle: Upright to nearly horizontal. Strength: Strong. Texture: Smooth, glabrous. Color: 145D.

*Reproductive organs.*—Androecium: None observed. Gynoecium: Only observed on disc florets. Pistil length: About 1.1 cm. Stigma shape: Two-parted. Stigma color: 23A. Style length: About 9 mm. Style color: 1C. Ovary color: 157D.

*Seed/fruit.*—Seed and fruit production has not been observed.

Disease/pest resistance: Resistance to pathogens and pests common to *Gazanias* has not been observed on plants grown under commercial conditions.

Garden performance: Plants of the new *Gazania* have been observed to have good garden performance and to tolerate wind, rain and temperatures from about 0° C. to about 32° C.

It is claimed:

1. A new and distinct *Gazania* plant named 'Suga119' as illustrated and described.

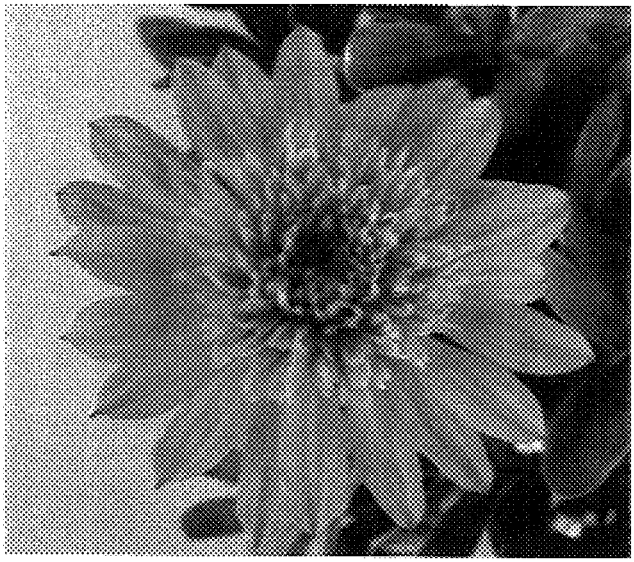
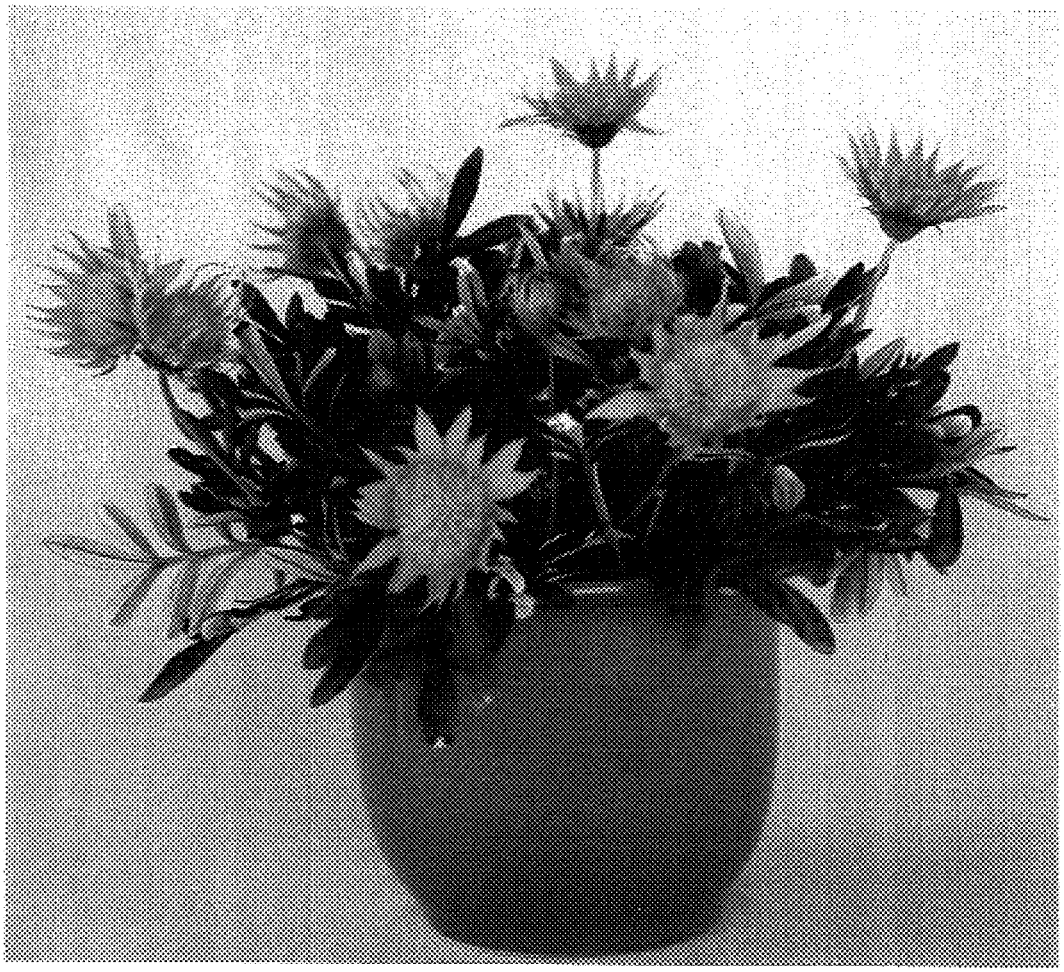

* * * * *